United States Patent
Videen et al.

(10) Patent No.: US 7,920,262 B2
(45) Date of Patent: Apr. 5, 2011

(54) SYSTEMS FOR MEASURING BACKSCATTERED LIGHT USING ROTATING MIRROR

(75) Inventors: Gorden W. Videen, Silver Spring, MD (US); Karri Olavi Muinonen, Tuusula, FL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 217 days.

(21) Appl. No.: 12/211,918

(22) Filed: Sep. 17, 2008

(65) Prior Publication Data

US 2010/0067007 A1 Mar. 18, 2010

(51) Int. Cl.
*G01N 21/00* (2006.01)
(52) U.S. Cl. .................. 356/342; 356/4.01; 356/5.01
(58) Field of Classification Search .............. 356/4.01, 356/5.01, 342
See application file for complete search history.

(56) References Cited

U.S. PATENT DOCUMENTS

| | | |
|---|---|---|
| 3,011,166 A | 11/1961 | Fell et al. |
| 4,067,009 A | 1/1978 | Constant |
| 4,164,740 A | 8/1979 | Constant |
| 4,269,518 A * | 5/1981 | Rahn ............................ 356/445 |
| 4,280,127 A | 7/1981 | Lee et al. |
| 4,553,144 A | 11/1985 | Houdard et al. |
| 4,616,227 A | 10/1986 | Homma et al. |
| 4,827,263 A | 5/1989 | Jones et al. |
| 4,929,950 A | 5/1990 | Freeman et al. |
| 4,963,877 A | 10/1990 | Wood et al. |
| 5,007,721 A | 4/1991 | Morris et al. |
| 5,184,133 A | 2/1993 | Tsao |
| 5,598,263 A * | 1/1997 | Safa ................................ 356/342 |
| 5,608,404 A | 3/1997 | Burns et al. |
| 5,926,125 A | 7/1999 | Wood |
| 6,150,972 A | 11/2000 | Bickel et al. |
| 6,222,933 B1 | 4/2001 | Mittermayer et al. |
| 6,377,167 B1 | 4/2002 | Juds et al. |
| 6,388,606 B1 | 5/2002 | Keydel et al. |
| 6,417,926 B1 | 7/2002 | Farhadiroushan et al. |
| 6,429,804 B1 | 8/2002 | Kishida et al. |
| 6,441,772 B1 | 8/2002 | Hellsten et al. |
| 6,563,451 B1 | 5/2003 | Krikorian et al. |
| 6,750,809 B1 | 6/2004 | Cho et al. |
| 7,030,968 B2 * | 4/2006 | D'Aligny et al. ............ 356/5.01 |
| 7,545,485 B2 * | 6/2009 | Okada et al. .................. 356/4.01 |
| 2007/0024845 A1 * | 2/2007 | Essling et al. ............. 356/141.4 |

OTHER PUBLICATIONS

Michael Mishchenko, "On the Nature of the Polarization Opposition Effect Exhibited by Saturn's Rings", pp. 351-361, The Astrophysical Journal 411, 1993.
Gordon Videen, "Polarization Opposition Effect and Second-Order Ray Tracing", pp. 5115-5121. Applied Optics, vol. 41, Issue 24, Aug. 2002.

(Continued)

*Primary Examiner* — Roy Punnoose
(74) *Attorney, Agent, or Firm* — Christos S. Kyriakou; Alan I. Kalb

(57) ABSTRACT

A system for measuring backscattered light from a sample is given. Light is output from a light source towards a rotating mirror, and then reflected by the rotating mirror towards the sample. The sample reflects backscattered light back towards the rotating mirror, which, having moved during the time it took for the light to propagate from the mirror to the sample and back, reflects the backscattered light to a detector located at a physical separation from the light source. The detected backscattered light may be analyzed to determine various properties of the sample.

7 Claims, 3 Drawing Sheets

OTHER PUBLICATIONS

Karri Muinonen, "Coherent Backscattering of Light by Complex Random Media of Spherical Scatterers: Numerical Solution", pp. 365-388, Institute of Physics, Publishing Waves Random Media 14, 2004.

Karri Muinonen, Coherent Backscattering by Solar System Dust Particles; pp. 271-296; Asteroids, Comets and Meteors; 1993.

M.I. Mishchenko; Polarization Effects in Weak Localization of Light: Calculation of the Copolarized and Depolarized Backscattering Enhancement Factors; 4 pages; The American Physical Society, vol. 44-22, 1991.

Michael Mishchenko; Full Angular Profile of the Coherent Polarization Opposition Effect; pp. 888-891; Journal Optical Society of America. vol. 17, No. 5; May 2000.

Karri Muinonen; Scattering of Light by Solar System Dust: The Coherent Backscatter Phenomenon; pp. 12-15; Proceedings of the Finnish Astronomical Society, Helsinki; 1990.

E. Zubko, Yu. Shkuratov, G. Videen, and N. N. Kiselev, 2006: DDA simulations of light scattering by small irregular particles with various structure, J. Quant. Spectrosc. Radiative Transfer 101, 416-434.

E. Zubko, Y. Shkuratov, K. Muinonen and G. Videen, 2006: Collective effects by agglomerated debris particles in the backscatter. J. Quant. Spectrosc. Radiative Transfer 100, 489-495.

G. Videen, A. Wetmore, M. Petre and Y. Shkuratov, 2006: Analytic description of enhanced backscattering and negative polarization from a cloud of dipoles. J. Quant. Spectrosc. Radiative Transfer 100, 406-414.

E. Zubko, Y. Shkuratov, G. Videen, 2006: Discrete-dipole analysis of backscatter features of agglomerated debris particles comparable in size with wavelength. J. Quant. Spectrosc. Radiative Transfer 100, 483-488.

E. Zubko, Y. Shkuratov, G. Videen, 2004: Coherent backscattering effect for non-zero elements of mueller matrix of discrete media at different illumination-observation geometries, J. Quant. Spectrosc. Radiative Transfer 89, 443-452.

E. Zubko, Y. Shkuratov, M. Hart, J. Eversole, and G. Videen, 2004: Backscattering of aggolmerate particles J. Quant. Spectrosc. Radiative Transfer 88, 163-172.

E. Zubko, Y. Shkuratov, M. Hart, J. Eversole, and G. Videen, 2003: Backscattering and negative Polarization of agglomerate particles. Opt. Lett. 28, 1504-1506.

* cited by examiner

SYSTEMS FOR MEASURING BACKSCATTERED LIGHT USING ROTATING MIRROR

GOVERNMENT INTEREST

The invention described herein may be manufactured, used, and licensed by or for the United States Government.

BACKGROUND

1. Technical Field

The disclosure generally relates to light scattering, detection, and characterizing particle systems.

2. Description of the Related Art

Light scattering can provide a non-destructive means of obtaining information about an object from a distance. As use herein, the term "light" refers to electromagnetic radiation over the entire electromagnetic spectrum including, but not limited to, visible light, ultraviolet light, infrared light, and near infrared light. The object can be a surface, like that of the Earth observed from space or of a computer wafer in a cleanroom environment. The object can also be a cloud consisting of smoke, ice crystals, pollutants, biological agents, or any number of other things about which information is desired. In many scattering configurations, the light source and detector are in close proximity. For instance, in monitoring the atmosphere for a cloud of particles using Light Detection and Ranging (LIDAR), a laser and a detector located on the same apparatus are used. This is primarily for convenience, as it requires only one physical station to set up for instrumentation. In addition, for observations from a distance it makes alignment much simpler. When the source and the detector are each separate instruments, they cannot simultaneously detect and receive light at the same location as there is always some physical separation between them; therefore, the light that scatters from the object of interest cannot be measured by the detector in the exact backscatter direction, which is located 180 degrees from forward scatter. It is measured at some finite angle $\beta$, the backscatter angle, measured from the exact backscatter direction. This finite angular extent can have implications in the interpretation of the resulting data.

Various physical phenomena occur when light traveling from a source to an object is scattered back in the direction of the source, i.e., in the backscatter region. In sensing terrain, for instance, no shadows are seen in the exact backscatter direction, but as $\beta$ increases, shadows will become visible that will reduce the signal on the detector. This is sometimes referred to as the shadowing effect. This shadowing contains information on the morphology and polydispersity of the particles in the sample. In addition, multiple scattering of rays by points on the object causes the rays to interfere with each other. In the backscatter region, rays that travel reciprocal paths interfere constructively, resulting in an increase in signal intensity on the detector. This is sometimes referred to as the coherent backscattering effect or backscattering surge. Accompanying the coherent backscattering effect is the polarization opposition effect—light has zero polarization in the exact backscatter region, but has a negative polarization state at angles slightly off the exact backscatter direction The amount of signal intensity increase in the backscatter region and the rate of fall-off of the polarization are determined by the morphological and chemical properties of the object; hence, a measurement of these light-scattering properties contains important information about the object.

The properties of the absolute intensity and rate of change of intensity and polarization state in the backscatter region are of interest for characterizing objects. Most remote-measuring techniques like LIDAR do not measure light in the exact backscatter direction ($\beta=0$), so it is difficult to interpret the information that is retrieved. In addition, it is desirable to know the scattering properties as a function of backscatter angle $\beta$, i.e. to have measurements at multiple angles across the backscatter region. One way of decreasing the angle $\beta$ is to make the distance to the object extremely large or to reduce the distance between the source and the detector; however, $\beta$ still remains finite.

SUMMARY

Systems for measuring backscattered light are provided. In this regard, an exemplary embodiment of a system comprises the following: a light source operative to output light; a mirror, operative to rotate with a rotational frequency, such that the light from the light source is reflected by the mirror toward the sample and backscattered light, corresponding to the light from the light source and scattered from the sample, is reflected by the mirror; and a detector operative to receive the backscattered light reflected from the mirror.

Other systems, methods, features and/or advantages of this disclosure will be or may become apparent to one with skill in the art upon examination of the following drawings and detailed description. It is intended that all such additional systems, methods, features and/or advantages be included within this description and be within the scope of the present disclosure.

BRIEF DESCRIPTION OF THE DRAWINGS

Many aspects of the disclosure can be better understood with reference to the following drawings. The components in the drawings are not necessarily to scale. Moreover, in the drawings, like reference numerals designate corresponding parts throughout the several views.

DETAILED DESCRIPTION

Systems for measuring backscattered light are provided, and several exemplary embodiments will be discussed in detail. In this regard, embodiments may be used for measuring the spatial relationship between objects at a distance. Additionally or alternatively, some embodiments may be used to provide information about the size distribution and/or chemical properties of particles in a sample.

Figure 1A:
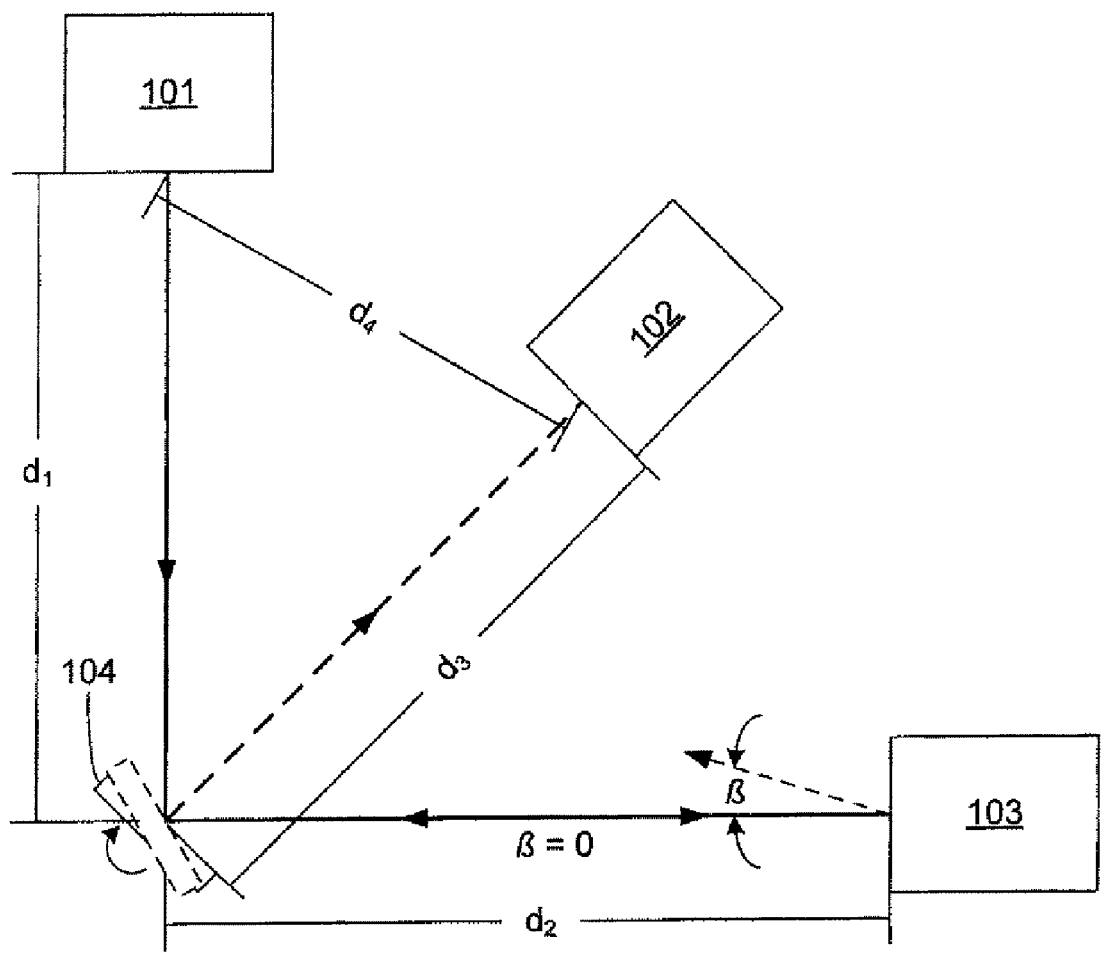
FIG. 1A shows an exemplary embodiment of a system for measuring backscattered light.

FIG. 1A shows an exemplary embodiment of a system for measuring backscattered light that incorporates a light source 101, a rotating mirror 104, and a detector 102. The mirror 104 rotates at a rotational frequency f. Light from the source 101 is directed to the mirror 104, which reflects the light toward a sample 103. The sample 103 scatters the light. The exactly backscattered ($\beta=0$) light propagates back toward the mirror 104. During the time interval in which the light propagates to the sample and back to the mirror, mirror 104 has rotated. Thus, the mirror is positioned to reflect the exactly backscattered light ($\beta=0$) to the detector 102 instead of back to the source 101. Notably, the detector is positioned to correspond to the range of the sample and the rotation frequency of the mirror. In this way, the light in the exact backscatter region may be measured. In some embodiments, the rotational frequency of the mirror is adjustable to reflect the backscattered light at different backscattering angles to the detector.

The detector 102 may obtain measurements for a range of values of backscatter angle β. In one embodiment, this is achieved by varying the rotational speed f of the mirror 104. As the rotational speed of the mirror varies, the amount of rotation of the mirror that occurs while the light propagates from the mirror to the sample and back to the mirror also varies, resulting in backscattered light with varying values of β being reflected to the detector. The backscattering angle β at a detector 102, located at distance $d_4$ from the source 101, is given by $\beta \sim (d_4 - 8\pi f d_3 d_3/c)/(d_2+d_3)$, where f is the rotational frequency of the mirror 104, $d_2$ is the distance between mirror 104 and sample 103, c is the speed of light, and $d_3$ is the distance between detector 102 and mirror 104.

Figure 1B:
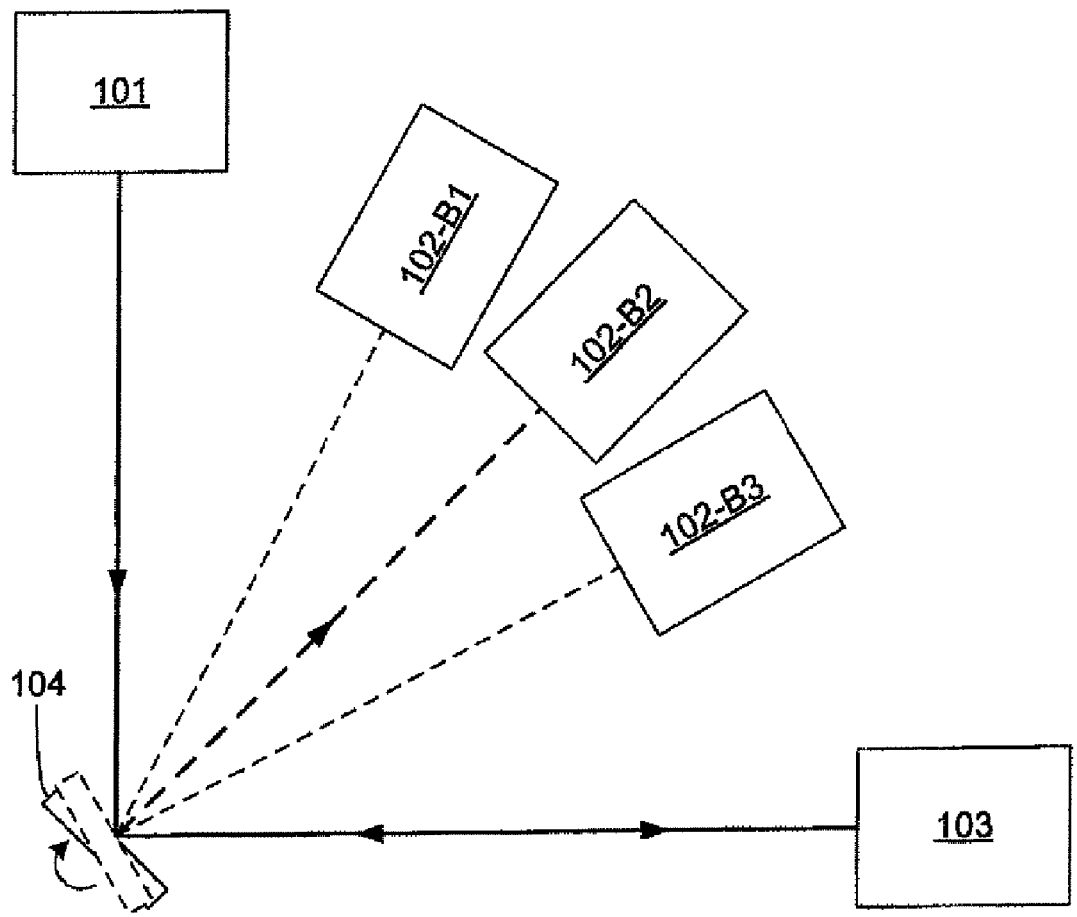
FIG. 1B shows another exemplary embodiment of a system for measuring backscattered light.

In another embodiment, shown in FIG. 1B, multiple detectors 102-B1, 102-B2, and 102-B3 are positioned in multiple locations in the backscatter region; these locations correspond to different values of β. Alternatively, a single detector 102 may be moved to various locations across the backscatter region during operation, as shown by locations 102-B1, 102-B2, and 102-B3 in FIG. 1B. At each location backscattered light is measured for a different value of β, or, alternatively, different ranges of the sample for a given β. FIG. 1B is not limiting; the number of detectors and detector locations may vary depending on the application. As above, the backscattering angle β at any detector 102, located at distance $d_4$ from the source 101, is given by $\beta \sim (d_4 - 8\pi f d_2 d_3/c)/(d_2+d_3)$, where f is the rotational frequency of the mirror 104, $d_2$ is the distance between mirror 104 and sample 103, c is the speed of light, and $d_3$ is the distance between detector 102 and mirror 104.

In another embodiment, a pulsed laser with a frequency corresponding to the rotational frequency f of the mirror 104 is used as the source 101. The phase lag of the pulsed laser relative to rotational frequency f may be adjusted to scan across the sample 103 by timing the laser to reflect from the mirror at various points in the mirror's rotation, thereby illuminating different points on the sample. The detector may be a charge-coupled device (CCD) detector, which measures angular extent, in addition to exact backscattering. Also, the mirror may be of sufficiently high quality so as not to corrupt the state of the reflected light significantly. By way of example, a mirror exhibiting roughness $<\lambda/10$, where λ is the wavelength of the incident light, should be sufficient for most applications where the samples are irregular surfaces with roughness significantly greater than λ.

Some embodiments may be used for remote sensing, for example LIDAR. By way of example, in remote-sensing mode, the sample may be located a large distance $d_2$ from the mirror. Because of the large distance, the distance $d_1$ between the source and the rotating mirror may be made small, and it is possible to physically locate the source, detector, and mirror in one structure. In such an embodiment, the angle β is greatly reduced due to the relatively small size of the mirror in relation to the distance between the sample 103 and mirror 104. Other embodiments may be used for sample characterization; the sample in these embodiments is located a short distance $d_2$ from the mirror. Because of the small $d_2$, the distance $d_1$ between the mirror and the source must be relatively large. In this case, the angle β can be made large. In this embodiment, the device may comprise two physical apparatuses. The source and detection components may be located together in one structure, and the rotating mirror may be contained in a separate structure, as it should be a relatively large distance from the source and detection components.

Figure 2:
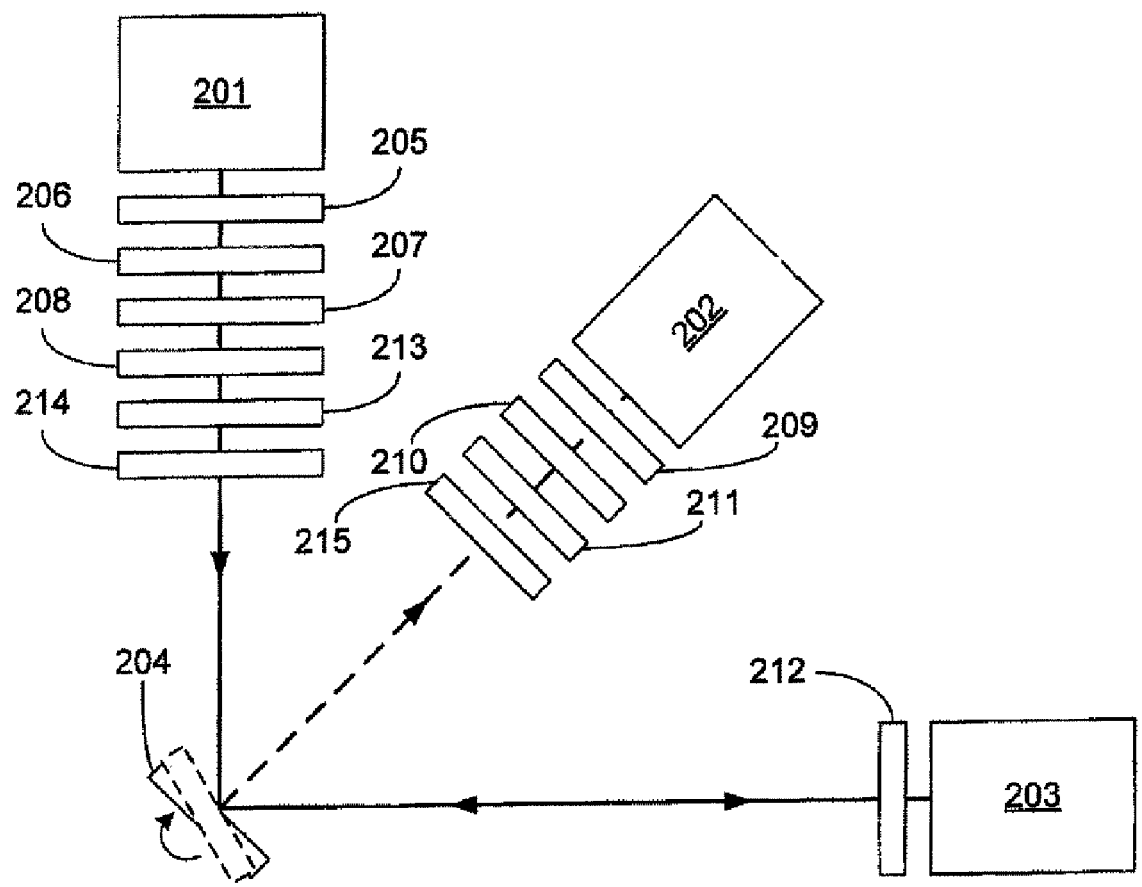
FIG. 2 shows another exemplary embodiment of a system for measuring backscattered light.

The light emitted from the source may be treated to reduce stray signals and ensure that angular divergence is reduced. FIG. 2 shows an embodiment of a system for measuring backscattered light using optics for this purpose. As shown in FIG. 2, the light emitted from source 201 is collimated by a spatial filter assembly 205, resulting in all the rays being incident on the sample. This reduces the divergence of the light, which tends to reduce the error in the measured backscatter angle. A diaphragm or field stop 208 adjusts the size of the illuminated area of the sample. Polarization filters 206 can be inserted at the source to control polarization characteristics of the light from the source. An optical modulator 207 is used to adjust the polarization state and also to modulate the light from the source to reduce noise. Polarizers or quarter-wave plates 213 and 212, can be placed in front of the source 201 and the sample 203, respectively, adjust the polarization state of the light. A lock-in amplifier 214 can be used to amplify the source signal; the phase of the lock-in amplifier may be adjusted in conjunction with the rotation frequency f of the mirror to scan across the sample and the backscatter region. Depending on the information sought regarding sample 203, various embodiments may comprise any combination of the forgoing optics to treat the light from the source 201.

Further embodiments have optics inserted at detector 202 to increase the signal-to-noise ratio or to detect light at particular polarization states. Again referring to FIG. 2, a diaphragm and lens 210 reduce stray light. The lens is preferably placed so that its focal point is on the detector plane, so that parallel rays of light are detected; i.e., light rays that are scattered in the same direction. A spatial filter assembly may be used in place of the diaphragm 208 and lens 210. A polarizer 211 may be included to select the polarization state of the detected light, allowing measurement of the intensity of a particular polarization state. A lock-in amplifier 209 may also be included to reduce the noise from external light sources; the lock-in amplifier may be modulated with the frequency f of the rotating mirror 204, with the pulse frequency of the source laser 201, or with an optical modulator 207 placed at the source 201 to scan across the sample. Apertures 215 may also be inserted at the detector to limit the field of view of the detector 202. Depending on the information sought regarding sample 203, various embodiments may comprise any combination of the forgoing optics to treat the light received at the detector 202.

Preferably, the light used in the present invention includes visible light, ultraviolet light or infrared light More preferably, the light is or includes visible light or infrared light. Most preferably, the light is or includes visible light or near infrared light.

It should be emphasized that the above-described embodiments are merely possible examples of implementations set forth for a clear understanding of the principles of this disclosure. Many variations and modifications may be made to the above-described embodiments without departing substantially from the spirit and principles of the disclosure. All such modifications and variations are intended to be included herein within the scope of this disclosure and protected by the accompanying claims.

The invention claimed is:

1. A system for measuring backscattered light from a sample, comprising:
   a light source operative to output light;
   a mirror, operative to rotate with a rotational frequency, such that the light from the light source is reflected by the mirror toward the sample and backscattered light, corresponding to the light from the light source and scattered from the sample, is reflected by the mirror;

a detector operative to receive the backscattered light reflected from the mirror and a spatial filter assembly located on an optical path between the light source and the mirror, the spatial filter assembly operative to collimate the light from the light source.

2. The system of claim 1, wherein the light source is a pulsed laser timed to correspond to the rotational frequency of the mirror.

3. The system of claim 2, wherein a phase lag of the pulsed laser is varied to scan across the sample.

4. A system for measuring backscattered light from a sample, comprising:
   a light source operative to output light;
   a mirror, operative to rotate with a rotational frequency, such that the light from the light source is reflected by the mirror toward the sample and backscattered light, corresponding to the light from the light source and scattered from the sample, is reflected by the mirror;
   a detector operative to receive the backscattered light reflected from the mirror and a polarizer located on an optical path between the light source and the mirror, the polarizer operative to adjust the polarization state of the light from the light source.

5. The system of claim 4, further comprising a quarter-wave plate located on an optical path between the light source and the mirror, the quarter-wave plate operative to adjust the polarization state of the light from the light source.

6. A system for measuring backscattered light from a sample, comprising:
   a light source operative to output light;
   a mirror, operative to rotate with a rotational frequency, such that the light from the light source is reflected by the mirror toward the sample and backscattered light, corresponding to the light from the light source and scattered from the sample, is reflected by the mirror;
   a detector operative to receive the backscattered light reflected from the mirror a diaphragm and lens, each of which are located on an optical path between the mirror and the detector, the diaphragm and lens operative to collimate the light
   and a spatial filter assembly located on an optical path between the mirror and the detector, the spatial filter assembly operative to collimate the light.

7. The system of claim 6, further comprising a polarizer located on an optical path between the mirror and the detector, the polarizer operative to adjust the polarization state of the light at the detector, allowing measurement of the intensity of a particular polarization state.

* * * * *